US012502530B2

(12) United States Patent
Golovac

(10) Patent No.: US 12,502,530 B2
(45) Date of Patent: Dec. 23, 2025

(54) ELECTROTHERAPEUTIC DEVICE

(71) Applicant: GOLOVAC CONSULTING LLC, Coral Gables, FL (US)

(72) Inventor: Stanley Golovac, Coral Gables, FL (US)

(73) Assignee: GOLOVAC CONSULTING LLC, Coral Gables, FL (US)

( * ) Notice: Subject to any disclaimer, the term of this patent is extended or adjusted under 35 U.S.C. 154(b) by 610 days.

(21) Appl. No.: 17/961,306

(22) Filed: Oct. 6, 2022

(65) Prior Publication Data

US 2024/0115853 A1 Apr. 11, 2024

(51) Int. Cl.
*A61N 1/00* (2006.01)
*A61N 1/05* (2006.01)

(52) U.S. Cl.
CPC .................................. *A61N 1/0558* (2013.01)

(58) Field of Classification Search
CPC .................................................... A61N 1/0558
See application file for complete search history.

(56) References Cited

U.S. PATENT DOCUMENTS

2011/0060395 A1* 3/2011 Cantlon ............... A61N 1/0509 607/116
2012/0185027 A1* 7/2012 Pianca ................... A61N 1/057 607/117
2018/0099147 A1* 4/2018 Kane .................. A61N 1/37518
2020/0179677 A1* 6/2020 Gerber ................. A61N 1/0558

* cited by examiner

*Primary Examiner* — Niketa Patel
*Assistant Examiner* — Anant A Gupta
(74) *Attorney, Agent, or Firm* — Buckingham, Doolittle & Burroughs, LLC

(57) ABSTRACT

An electrotherapeutic device includes a stimulation member and an anchor to retain the stimulation member at the treatment site of implantation. The stimulating member and the anchor have surfaces that are "keyed" to each other, such that when the stimulating member is inserted in the anchor, the stimulating member is resistant to moving relative to the anchor. The anchor also includes one or more retaining channels, which are configured to receive sutures therein that are used to secure the anchor to the treatment site of implantation, which prevent the anchor from moving or migrating relative to the treatment site.

4 Claims, 8 Drawing Sheets

ELECTROTHERAPEUTIC DEVICE

TECHNICAL FIELD

The various embodiments disclosed herein generally relate to medical devices. Particularly, the various embodiments disclosed herein relate to improved methods and devices for electrotherapeutic stimulation. More particularly, the various embodiments disclosed herein relate to an improved anchor for retaining an electrotherapeutic stimulating member at a treatment site of implantation during surgical implantation in a patient.

BACKGROUND

Electrotherapeutic stimulation, whereby electrical signals are applied to the target tissue of a patient, has been utilized as a therapy for the treatment of chronic pain for many years. One type of electrotherapeutic stimulation, referred to as neuromodulation, has been widely adopted, whereby targeted electrical stimulation signals delivered from implanted devices are utilized to achieve therapeutic intervention of the central, peripheral and autonomic nervous system. In fact, electrotherapeutic stimulation of the spinal cord, or spinal cord stimulation (SCS), has become one of the most established forms of neuromodulation used to treat neuropathic pain.

Neuropathic pain includes pain that is caused by a maladaptive response of nervous tissue to nerve injury of either the peripheral or central nervous system. Such neuropathic pain can exist independently of any form of tissue injury outside of the central nervous system. Many conditions may lead to neuropathic pain, including various diseases such as HIV, herpes, diabetes, cancer, and autoimmune disorders; acute trauma, including surgical procedures, physical injuries, and electric shock; chronic trauma, including repetitive motion disorders: and chemical toxicity resulting from alcohol, chemotherapy, or heavy metals, for example.

In addition to the therapeutic treatment of neuropathic pain, spinal cord stimulation (SCS) has also been used to treat ischemic pain syndromes. Ischemic pain syndromes encompass chronic critical limb ischemia, angina pectoris and other visceral pain syndromes, including chronic pancreatitis, chronic painful bladder syndrome, chronic abdominal pain, brachial plexus injuries, phantom limb pain and ischemic limb pain.

In the case of spinal cord stimulation (SCS), an electrical stimulator provides a plurality of electrodes that are coupled by an electrically conductive wire to receive electrical signals from a battery powered signal generator or control unit. The electrical stimulator is implanted within the patient's body near the spinal nerves of a particular treatment site that is the source of the pain. The precise position is the result of painstaking trial and error by the implanting surgeon, and therefore it is highly desirable that the stimulator be permanently retained in such position to maintain the desired therapeutic pain reducing response over time. Sutures are utilized to secure the electrical stimulator in place so that the electrodes are prevented from moving or migrating over time so that they are retained in a therapeutic region at or near the target treatment site of implantation. The signal generator supplies electrical signals to the electrodes of the electrical stimulator, which are then received by the spinal nerves that are in the vicinity. These electrical signals serve to interfere with the nerve impulses generated by the patient's body that communicate pain to their brain.

As a result, the patient's perception of pain is greatly diminished, thereby improving the patient's quality of life.

However, a major issue with current generation spinal cord stimulation (SCS) devices is that after implantation, the electrical stimulator migrates or moves from the desired treatment site of implantation. This unwanted migration of the electrical stimulator substantially degrades and impairs the ability of the SCS to relieve a patient's pain, which is unwanted. Such migration or movement of the electrical stimulator is due to the design of the electrical stimulator and the use of surgical thread to form sutures to secure the stimulator in place during implantation. Specifically, traditional electrical stimulators of current SCS designs have a smooth outer body surface in which one or more sutures are looped partially around the body of the stimulating and through insertion points in the tissue at the treatment site of implantation. In other words, the sutures secure the electrical stimulator, which includes the electrodes, to the tissue of the treatment site by applying a compressive force about a portion of the electrical stimulator. As such, the sutures that are in contact with the electrical stimulator are retained in place by friction that occurs between the suture itself and the smooth outer surface of the electrical stimulator. Unfortunately, due to the fluidic environment of the treatment site where the electrical stimulator is implanted, this friction is reduced, increasing the chances of unwanted movement, or migration, of the electrical stimulator over time, away from the desired position at the treatment site. The potential of this unwanted migration of the electrical stimulator is further increased given the movement of the patient, which inevitably alters and distorts the treatment site where the electrical stimulator is implanted, causing the electrical stimulator to be subject to various forces and trauma, which results in its movement or migration from its desired position.

The migration or movement of the SCS electrical stimulator provided by the SCS complicates a patient's treatment during and after the surgical implantation procedure. Migration also increases the patient's risk of infection and other adverse surgical events, as well as degrades the ability of the SCS to provide therapeutic pain reduction to the patient. In fact, such lead migration commonly occurs with approximately 11-17% of treated patients. Because the migration or movement of the electrical stimulator affects the ability of the SCS to effectively mitigate a patient's pain, revisionary surgeries to reposition the electrical stimulating are necessary. Unfortunately, such surgical revisions expose the patient to additional trauma, as well as life threatening complications and hazardous infection. Furthermore, if the patient's health status compromised, he or she may not be a candidate for repositioning the electrical stimulator by a revisionary surgery, and therefore they will have to suffer with increased pain.

Therefore, there is a need for an electrical stimulator or stimulating member having one or more electrodes, which is resistant to movement or migration from a treatment site of implantation. In addition, there is a need for an electrical stimulator that includes a keyed outer surface that is configured to mate with a retaining aperture in an anchor that also has a keyed surface, so as to prevent movement of the electrical stimulating member relative to the anchor when the anchor and the stimulating member are implanted. In addition, there is a need for an anchor that is formed of flexible material to facilitate implantation. In addition, there is a need for an anchor having one or more retention channels to receive and retain one or more sutures therein to make the anchor and the electrical stimulating member carried therein resistant to movement or migration after implantation at the treatment site.

SUMMARY

In light of the foregoing, it is a first aspect of the various embodiments disclosed herein to provide an anchor comprising an elongated body having at least one aperture, a retaining cavity in fluid communication with the aperture, and a retaining channel disposed on at least a portion of an outer surface of the body.

It is a further aspect of the of the various embodiments disclosed herein to provide a stimulating member comprising an elongated body; a plurality of control sections on the body, wherein at least one spaced section is disposed between each group of the control sections, wherein each control section has a shape that is different from a shape of the spaced section; and an electrode provided by each of the control sections.

It is yet another aspect of the various embodiments disclosed herein to provide a kit comprising an anchor, wherein the anchor includes an elongated body having at least one aperture; a retaining cavity in fluid communication with the aperture, wherein the retaining cavity has a first keyed shape; a retaining channel disposed on at least a portion of an outer surface of the body; and a stimulating member, wherein the stimulating member includes a plurality of electrodes, and wherein the stimulating member has a second keyed shape; wherein the first keyed shape of the anchor and the second keyed shape of the stimulating member are configured to mate together, whereby when the stimulating member is inserted into the aperture, the stimulating member is retained by the retaining cavity of the anchor.

BRIEF DESCRIPTION OF THE DRAWINGS

These and other features and advantages of the various embodiments disclosed herein will become better understood with regard to the following description, appended claims, and accompanying drawings, wherein:

DETAILED DESCRIPTION

Figure 1A:
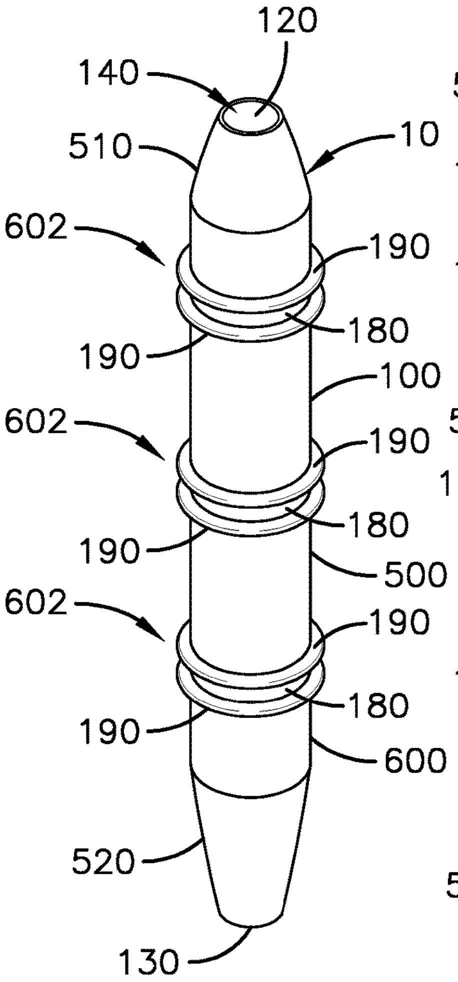
FIG. 1A is a perspective view of an anchor for retaining a stimulation member in accordance with the various embodiments disclosed herein.

An anchor and an electrotherapeutic stimulating member for providing electrotherapeutic pain relief treatment, in accordance with the various embodiments disclosed herein is referred to by numerals 10 and 12, respectively as shown in the various FIGS., particularly in FIGS. 1 and 2. The anchor 10, as shown in FIG. 1A, includes an elongated body 100 having substantially opposed openings 120 and 130, which leads to a retention cavity 140. The retention cavity 140 has a keyed surface 142 that has a shape or profile that is configured to be complementary to a keyed surface 160 of the stimulating member 12 that is received within the retention cavity 140. As such, the profile or shape of the keyed surface 142 of the retention cavity 140 and the keyed surface 160 of the electrical stimulating member 12 are complementary to each other, allowing them to be selectively locked together. Thus, the "keyed" relationship between the electrical stimulating member 160 and the retention cavity 140 serves to prevent the simulating member 160 from moving relative to the anchor 10. Disposed on the outer surface of the anchor 10 are one or more retaining channels 180, formed by projections 190. Thus, during implantation of the electrical stimulating member 160, the retaining channels 180 are configured to retain one or more sutures therein to secure the anchor 10 in place. It should be appreciated that while the discussion presented herein relates to the use of the anchor 10 and stimulating member 12 for application in a spinal cord stimulator (SCS), they may be used in any context or application.

I. Stimulating Member:

Specifically, the anchor 10 is configured to be used with the electrical stimulating member or stimulating member 12, as shown in FIG. 2. The stimulating member 12 is configured as an elongated member, having one or more individual electrically conductive electrodes 200 carried thereby. The stimulating member 12 includes a body 210 which defines therein a hollow cavity 220. In some embodiments, the body 210 of the stimulating member 12 may extend from an insertion end 240 as an elongated straight section 250, and then transitions to a curved section 260, and then extends to a base end 270, as shown in FIGS. 2A-B. As such, the insertion end 240 of the stimulating member 12 is configured to be inserted into the retaining cavity 140 of the anchor 10. However, it should be appreciated that the body 210 of the electrical stimulator member 12 may take on any desired shape, including a rectilinear shape, a curvilinear shape or a combination thereof. It should be appreciated that the hollow cavity 220 may be filled with any suitable dielectric material, such as plastic, so as to seal the components of the stimulating member 12 residing within the hollow cavity 220. In some embodiments, the end of the cavity 220 proximate to the insertion end 240 of the stimulating member 12 may contain an opening that is in fluid communication with the cavity 220, or in some embodiments, may be closed off.

The body 210 of the electrical stimulation member 12 may be formed from a rigid or semi-ridged material, which is electrically non-conductive (i.e. dielectric), such as plastic or composites thereof, for example. In some embodiments, the body 210 of the electrical stimulator member 12 may be formed of conformable material, such as conformable plastic or metal, including composites and alloys thereof, which can be bent into any desired shape. In the case of the use of a metal, to form the body 210, the electrodes 200 are isolated from the metallic body 210 by suitable dielectric members positioned between the electrodes 200 and the metallic body 210.

Figure 3:
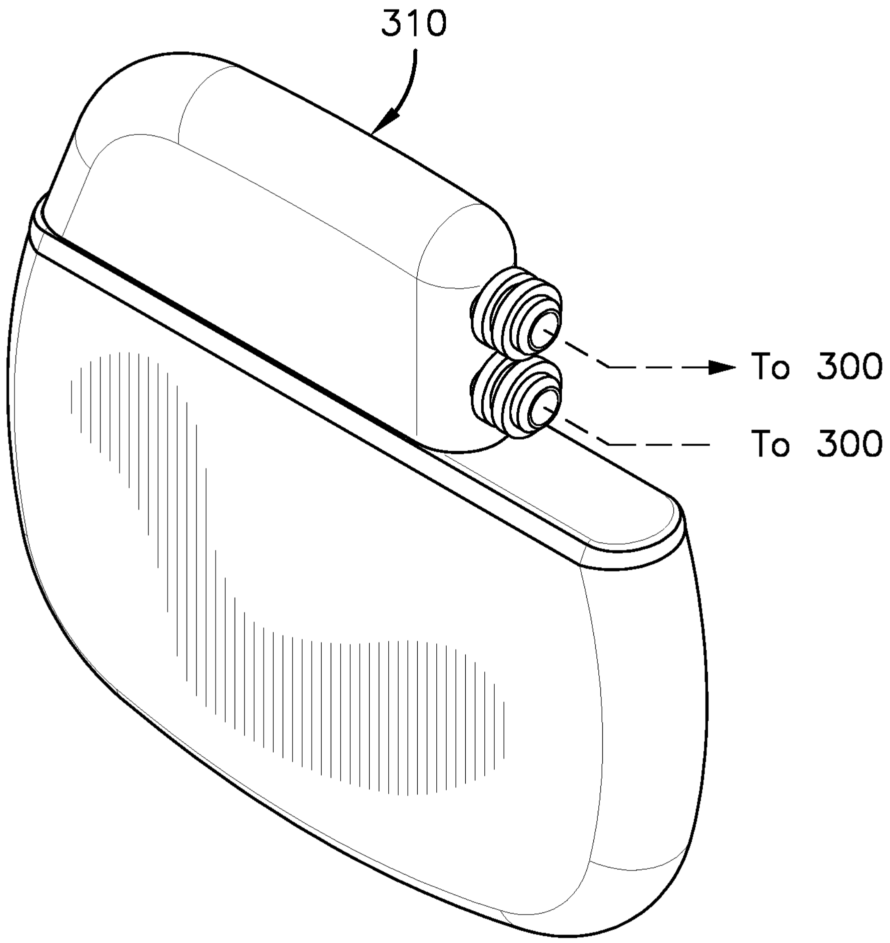
FIG. 3 is a perspective view of the control unit in accordance with the various embodiments disclosed herein.
Figure 5:
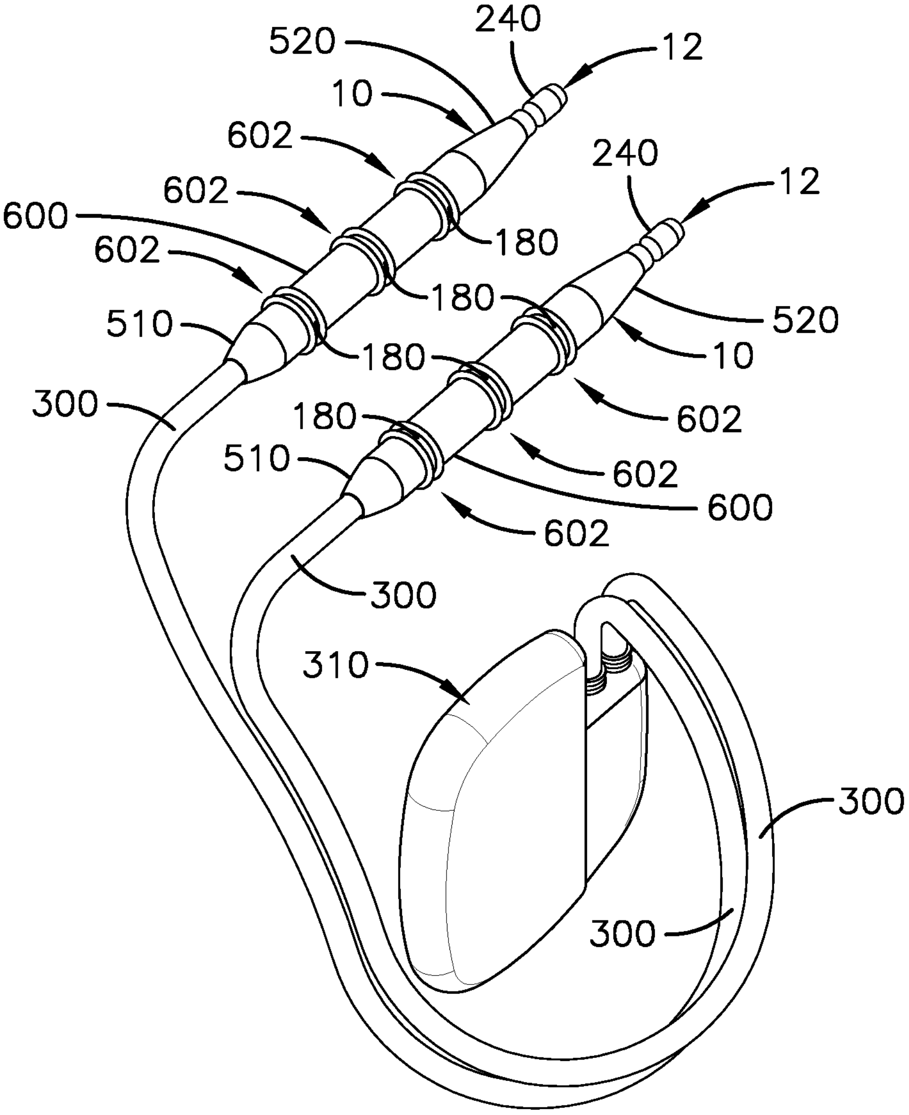
FIG. 5 is a perspective view of the control unit coupled to a plurality of stimulator members attached to anchors in accordance with the various embodiments disclosed herein.

The hollow cavity 220 of the stimulating member 12 carries a plurality of control wires 300 that connect the electrodes 200 to the control module or unit 310 shown in FIGS. 3 and 5. As such, the control wires 300 extend out of the hollow cavity 220 of the stimulating member 12, whereupon they exit therefrom through the base end 270. That is, one or more of the cylindrical segments 400 may include the electrode 200, wherein, each electrode 200 is attached to one of the control wires 300 at one end, while the other end of the control wire 300 extends out of the base end 270 of the stimulation member 12 and is attached to the control module 310. It should be appreciated that the control wires 300 extending out of the base end 270 are each individually encased in a section of dielectric material, such as plastic. In addition, in some embodiments, the group of multiple control wires 300 may be encased in another section of dielectric material, such as plastic.

The body 210 of the stimulating member 12 includes the keyed outer surface 160, having a profile or shape, which is configured to be complementary to the keyed surface 142 of the retention cavity 140 provided by the anchor 10. Disposed on the keyed outer surface 160 of the stimulating member 12 are the plurality of electrically conductive electrodes 200. Each of the electrodes 200 is coupled to the control wire 300 that is received through the hollow cavity 220, as previously discussed and as shown clearly in FIGS. 2C-D. It should be appreciated that the control wires 330 are attached to the electrodes 200 using any suitable means of fixation, such as soldering or welding for example. The electrodes 200 are configured in some embodiments to extend about the outer keyed surface 160 of the body 210 by 360 degrees. However, in other embodiments, the electrodes 200 may extend about the outer surface 160 of the body 210 by any amount, such as 270 degrees, 180 degrees, and 90 degrees for example.

Figure 2A:
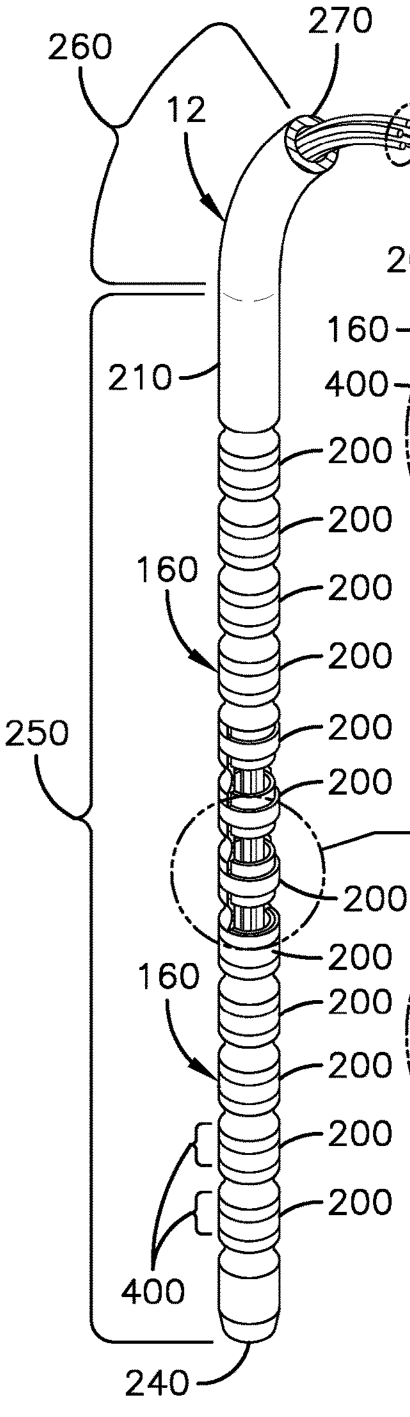
FIG. 2A is a perspective view of the stimulating member configured for use with the anchor in accordance with the various embodiments disclosed herein.
Figure 2C:
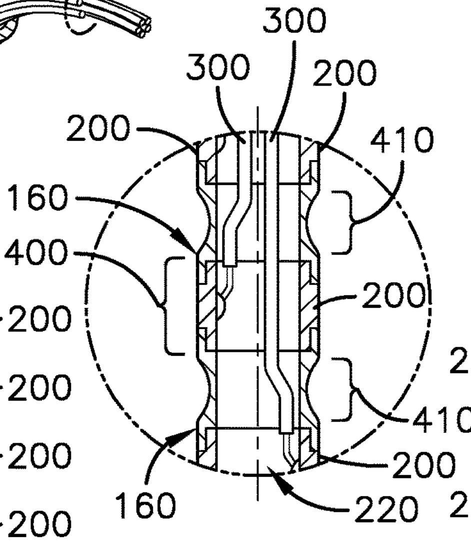
FIG. 2C is an inset view of the stimulating member shown in FIG. 2B in accordance with the various embodiments disclosed herein.
Figure 2D:
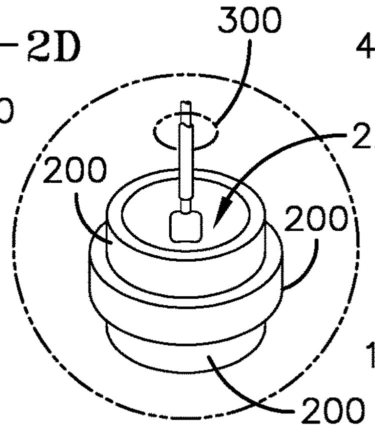
FIG. 2D is an inset view of the stimulating member shown in FIG. 2A in accordance with the various embodiments disclosed herein.
Figure 2B:
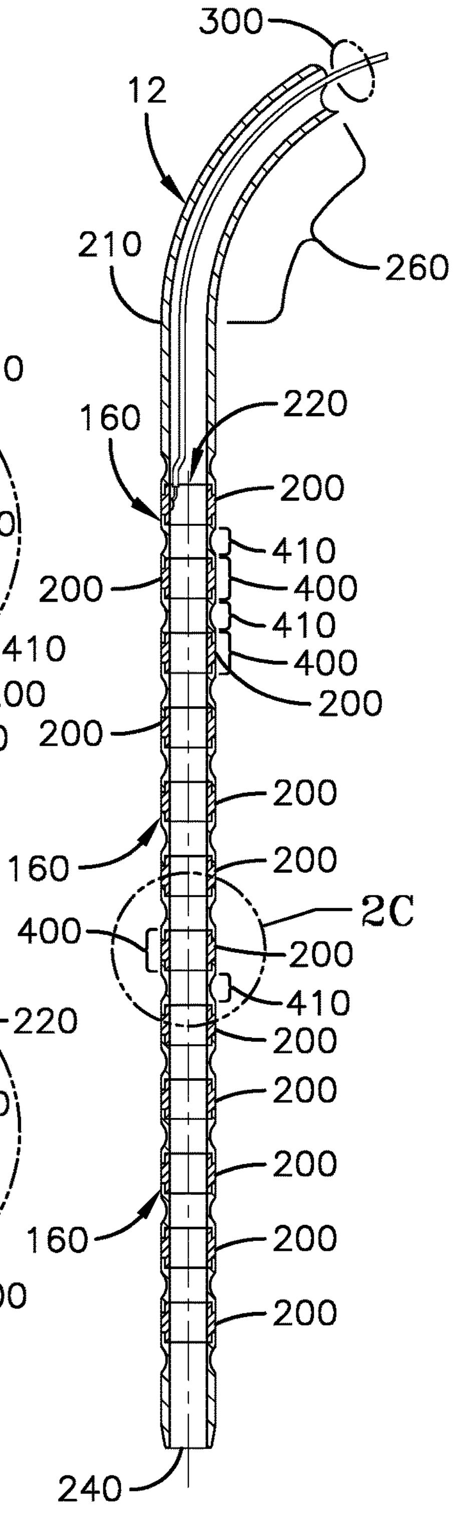
FIG. 2B is a cross-sectional view of the stimulating member in accordance with the various embodiments disclosed herein.

The keyed outer surface 160 of the body 210 of the stimulating member has profile or shape that is formed by a plurality of segments having one or more shapes. For example, as shown in FIGS. 2A-B, the keyed outer surface 160 of the stimulating member 12 is comprised of cylindrical segments or sections 400 (i.e. control sections or segments), in which each pair of cylindrical segments 400 is spaced apart by an annular concave segment or section 410 (i.e. spaced section or segment), as shown clearly in FIGS. 2A-C. It should be appreciated, however that the cylindrical segments 400 may be replaced by segments having a different shape, such as a concave shape, a convex shape, or a shape that is a combination of both. Furthermore, the annular concave segments 400 may be replaced by segments having a curvilinear shape, a rectilinear shape or a combination thereof. As such, the keyed outer surface 160 of the body 210 has a profile or shape that is complementary with the keyed surface 142 of the retention aperture 140 of the anchor 10, so as to be selectively retained thereto. That is, when the insertion end 240 of the stimulating member 12 is inserted into the retaining cavity 140 of the anchor 10, the keyed surfaces 142 and 160 are configured lockingly mate together, such that the stimulating member 12 resists or does not move relative to the anchor 10. However, it should be appreciated that the mating of the keyed surfaces 142 and 160 may be configured such that upon the application of a threshold amount of force, that the stimulating member 12 may be removed from the anchor 10.

As previously discussed, in the case of the SCS, the electrodes 200 of the stimulating member 12 is coupled by the electrically conductive control wires 300 to the control unit 310. The control module 310 is portably powered, such as by a battery, and generates suitable stimulation signals, which are carried by the control wires 300 to the one or more electrodes 200 provided by the stimulation member 12. Because each of the electrodes 200 is independently coupled by the control wire 300 to the control module 310, the electrodes 200 can be independently controlled to be either an anode or cathode to generate a stimulating path that extends between any of the two electrodes 200.

II. Anchor:

The anchor 10 includes the body 100 having a main section 500, which is terminated at each end by tapered ends 510 and 520. The main section 18 may be substantially cylindrical, as shown in the FIG. 1, however it may be any suitable shape. In the embodiment shown, the main section 500 is elongated, but is not required. It should be appreciated that the tapered ends 510 and 520 may have the same or different amounts, angles, or lengths of taper. For example, as shown in FIG. 1, the tapered end 520 may be longer than the tapered end 510. Positioned proximate to each tapered end 510 and 520 are respective openings 120 and 130, which open into the retention cavity 140. As such, the openings 120, 130 and the retaining cavity 140 are in fluid communication with each other. The anchor 10 is formed of any suitable material, such a flexible material, including material, such as elastomeric material.

Figure 4A:
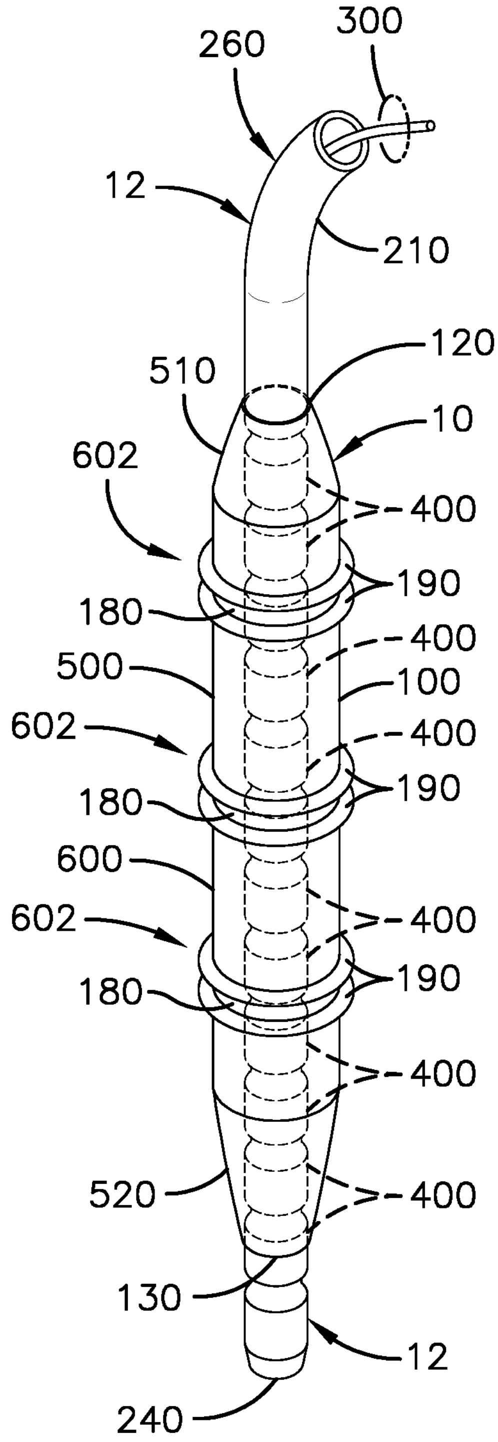
FIG. 4A is a perspective view of the stimulating member attached to the anchor in accordance with the various embodiments disclosed herein.
Figure 4B:
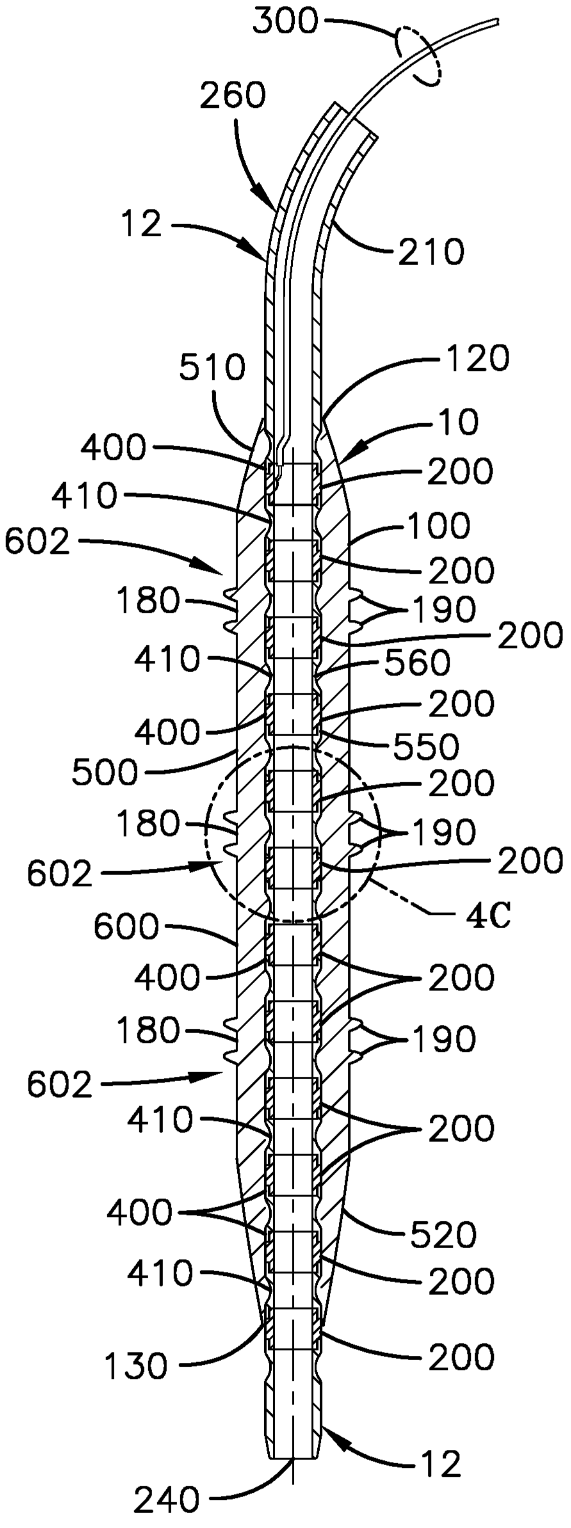
FIG. 4B is a cross-sectional view showing the stimulating member attached to the anchor in accordance with the various embodiments disclosed herein.
Figure 4C:
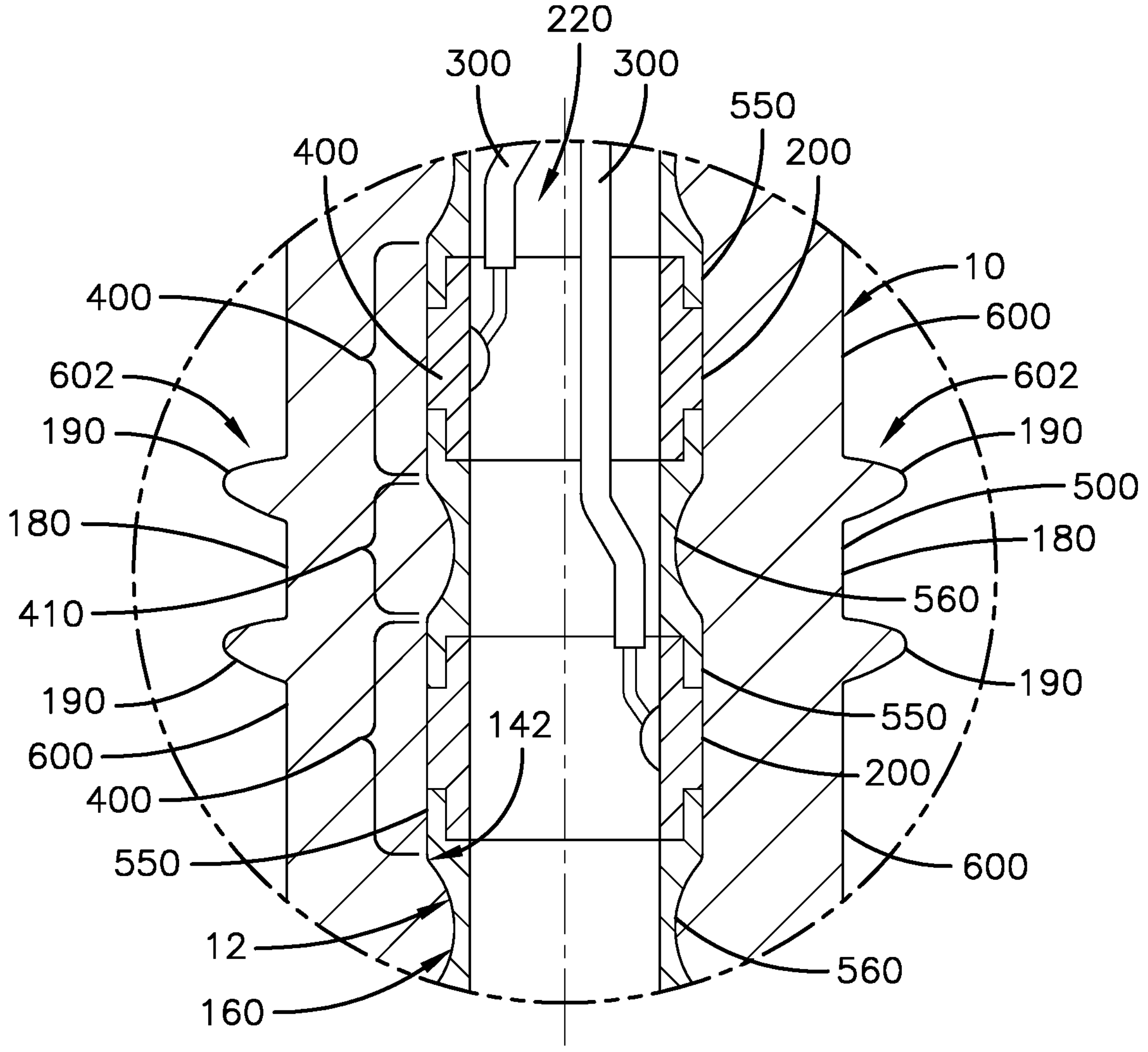
FIG. 4C is an inset view of FIG. 4B in accordance with the various embodiments disclosed herein.

The retention cavity 140 is configured to include the keyed surface 142, which is shaped or profiled so as to be complementary to the keyed outer surface 160 forming of the stimulation member 12. As such, due to these "keyed" surfaces 142 and 160, the stimulation member 12 is mated and retained within the complementary shape of the retaining cavity 140 after the stimulation member 12 is inserted therein, as shown in FIGS. 4A-C. This prevents the stimulation member 12 from moving relative to the anchor 10. It should be appreciated that the keyed surface 140 of the retaining cavity 140 may comprise a cylindrical cavity section/segment 550 (i.e. control cavity section/segment) and an annular convex cavity section/segment 560 (i.e. spaced cavity section/segment), which alternate along the length of the retaining cavity 140 of the anchor 10. For example, the cylindrical cavity section/segment 550 may have any shape, including a rectilinear shape, a curvilinear shape, or a shape that is a combination thereof. In addition, the annular convex cavity section/segment 560 may have any shape, including a rectilinear shape, a curvilinear shape, or a shape that is a combination thereof.

Because the keyed surface 160 of the stimulation member 12 and the keyed surface 142 of the retention cavity 140 of the anchor 10, are complementary to each other, the cylindrical segments 400 (i.e. control segment/section) and the concave segments 410 (i.e. spaced segment/section) of the keyed surface 160 of the stimulation member 12 are configured to respectively mate or fit within the cylindrical cavity segment 550 (i.e. control cavity segment/section) and the annular convex cavity segment 560 (i.e. spaced cavity segment/section) of the retaining cavity 140, as shown in FIGS. 4A-C. As a result, the stimulating member 12 is retained within the retaining cavity 140 of the anchor 10, thus preventing the stimulating member 12 from moving relative to the anchor 10. However, it should be appreciated that the keyed surface 160 of the stimulating member 12 and the keyed surface 142 of the retention cavity 140 may utilize any complementary shape so that the stimulating member 12 and the retaining cavity 140 of the anchor 10 can be mated together, so as to retain the stimulating member 12 to the anchor 10. It should be appreciated that the anchor 10 and the stimulating member 12 may use any number of shapes, designs, profiles to define their complementary keyed surfaces.

Figure 1B:
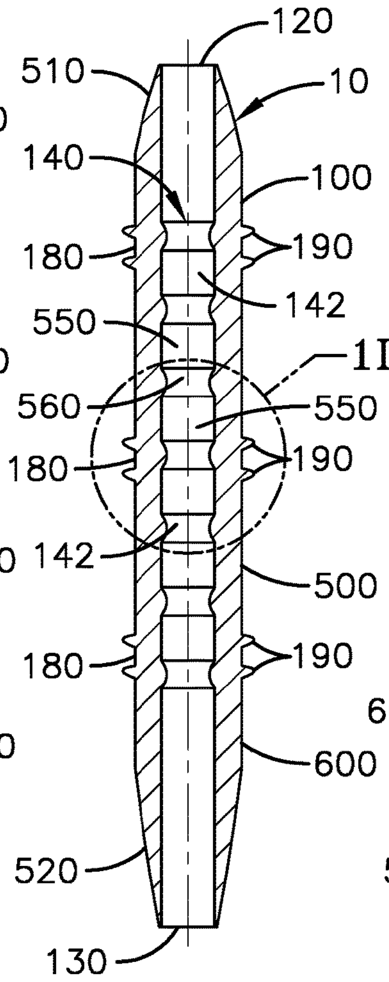
FIG. 1B is a cross-sectional view of the anchor in accordance with the various embodiments disclosed herein.

Disposed on an outer surface 600 of the anchor 10 are one or more sets 602 of spaced protrusions 190, as shown in FIGS. 1A-B. Each set 602 of the spaced apart protrusions 190 extend or protrude from the outer surface 600 of the anchor 10 and form the channel 180 therebetween. In some embodiments, the spaced sets of protrusions 190 may comprise annular members, such as rings, as shown in FIGS. 1A-B, that circumscribe the anchor 10.

It should be appreciated that each protrusion 190 of a given set 602 may be spaced apart so that the channel 190 formed has any suitable width, such as the width of the surgical thread used to form the sutures used to secure the anchor 10 to the treatment site. Furthermore, the sets 602 of protrusions 190 may be spaced apart by any suitable distance. In addition, any number of sets 602 of protrusions 190 may be used, such as 3 in case of the embodiment shown in the FIGS.

Figure 1C:
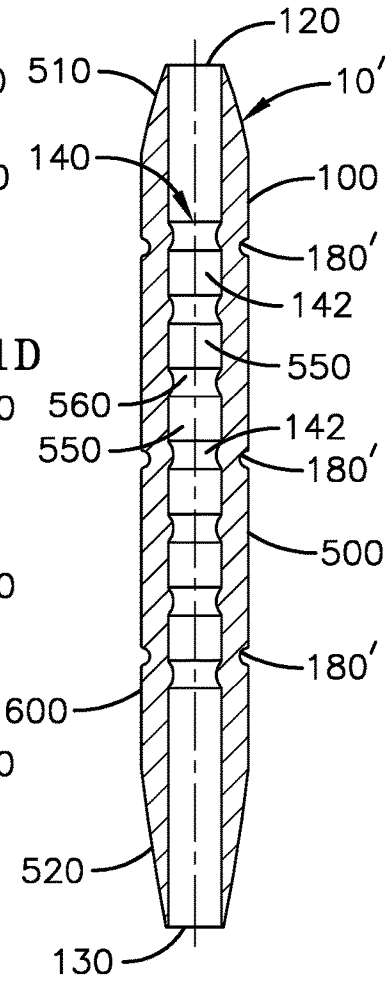
FIG. 1C is a cross-sectional view of an alternative anchor in accordance with the various embodiments disclosed herein.
Figure 1D:
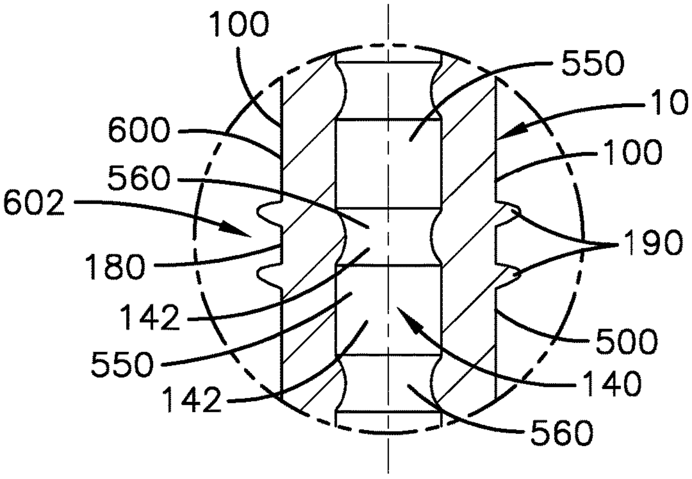
FIG. 1D is an inset view of FIG. 1B in accordance with the various embodiments disclosed herein.

In an alternative embodiment of the anchor, identified by reference numeral 10', as shown in FIG. 1C, the channels 180' are not defined by the protrusions 190 that extend above the outer surface 600 of the body 100 of the anchor 10, but rather the one or more channels 180' are disposed in the outer surface 600 of the body 100 of the anchor 10. As such, the channels or grooves 180' are disposed in the outer surface 600 of the body 100 and may have any suitable cross-sectional shape such as a curvilinear shape, a rectilinear shape, or a shape that is a combination thereof. It should be appreciated that in some embodiments that the channels 180' may extend about the main section 100 of the anchor 10, however, the channels 180' may be positioned anywhere along the outer surface 600 of the anchor 10, including on the tapered ends 510, 520. It should be appreciated that the channels 180 may have any suitable cross-sectional shape, such as a round, oval, square or rectangular cross-section. That is, the channels 180' may have a rectilinear shape, a curvilinear shape or a shape that is a combination of both. It should also be appreciated that while the channels 180' are shown to extend fully around or circumscribe the body 100 of the anchor 10 by 360 degrees, the channels 180' may partially extend about or partially circumscribe the body 100 by any suitable amount, such as 90, 180 or 270 degrees for example.

It should be appreciated that each channel 180' may have any suitable width, such as the width of the surgical thread used to form the sutures used to secure the anchor 10 to the treatment site. Furthermore, when a plurality of channels 180' are utilized, they may be spaced apart by any suitable distance. In addition, any number of channels 180' may be used, such as 3 in case of the embodiment shown in FIG. 1C.

In some embodiments of the anchor 10 it is contemplated that the internal diameter of the retaining cavity 140 is about 1.45 mm, while the stimulating member has an outer diameter of about 1.4 mm. In addition, the cylindrical cavity 550 of the anchor 10 may be about 1.5 mm in length and are spaced apart by the convex cavity 550 by about 2.5 mm. Similarly, the cylindrical segment 400 of the stimulator 12 may be about 1.5 mm in length and are spaced apart by the convex segment 410 by about 2.5 mm. In addition, the retaining cavity 140 may be about 30 mm in length. While this is one arrangement for providing the anchor 10 and the stimulating member, it should not be construed as limiting as any suitable dimension and arrangement of anchor 10 and the stimulating member 12 may be utilized.

Figure 6:
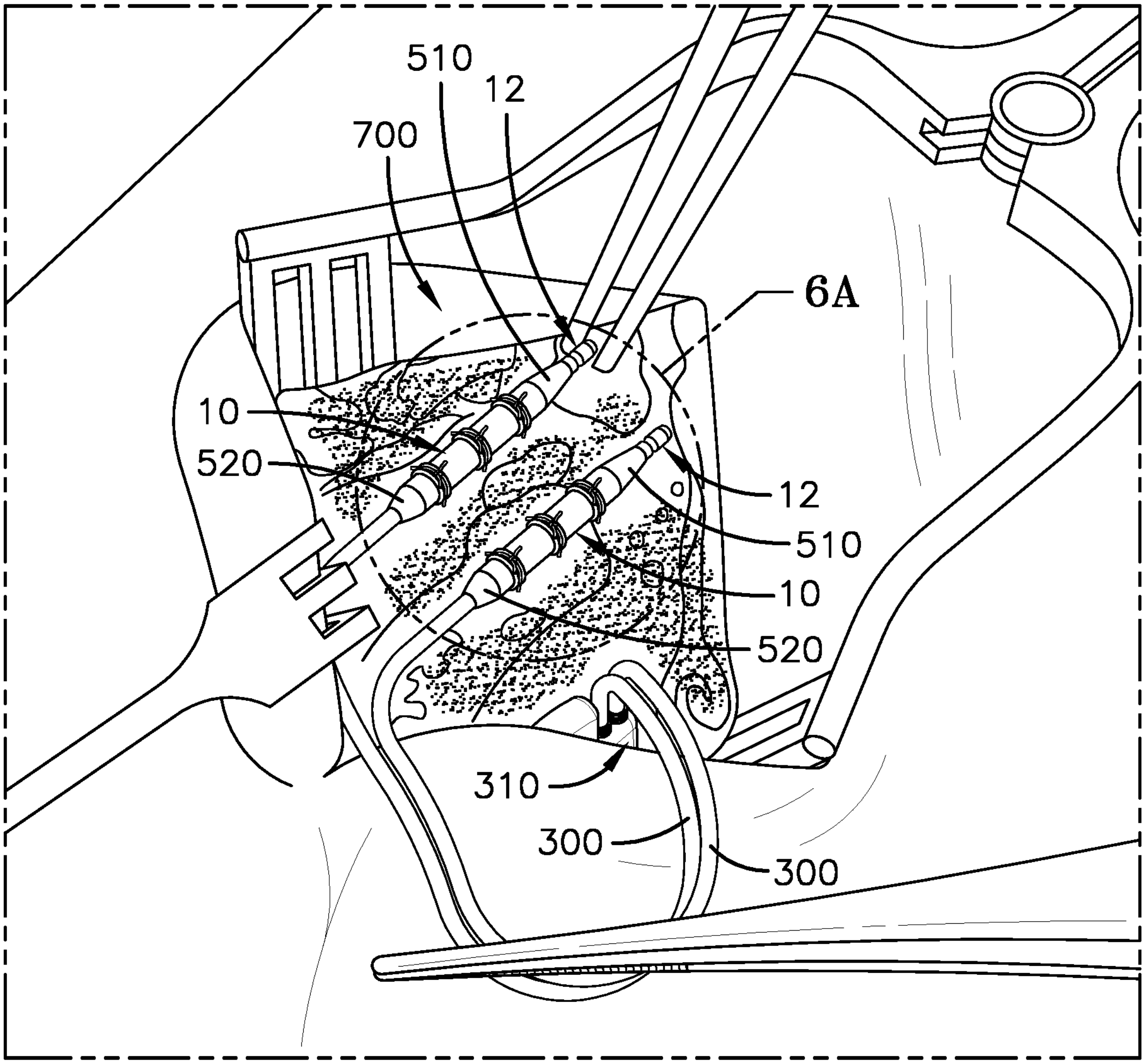
FIG. 6 is a perspective view showing multiple stimulating members attached to anchors, whereby the anchors are sutured to tissue at the treatment site of implantation in accordance with the various embodiments disclosed herein.
Figure 6A:
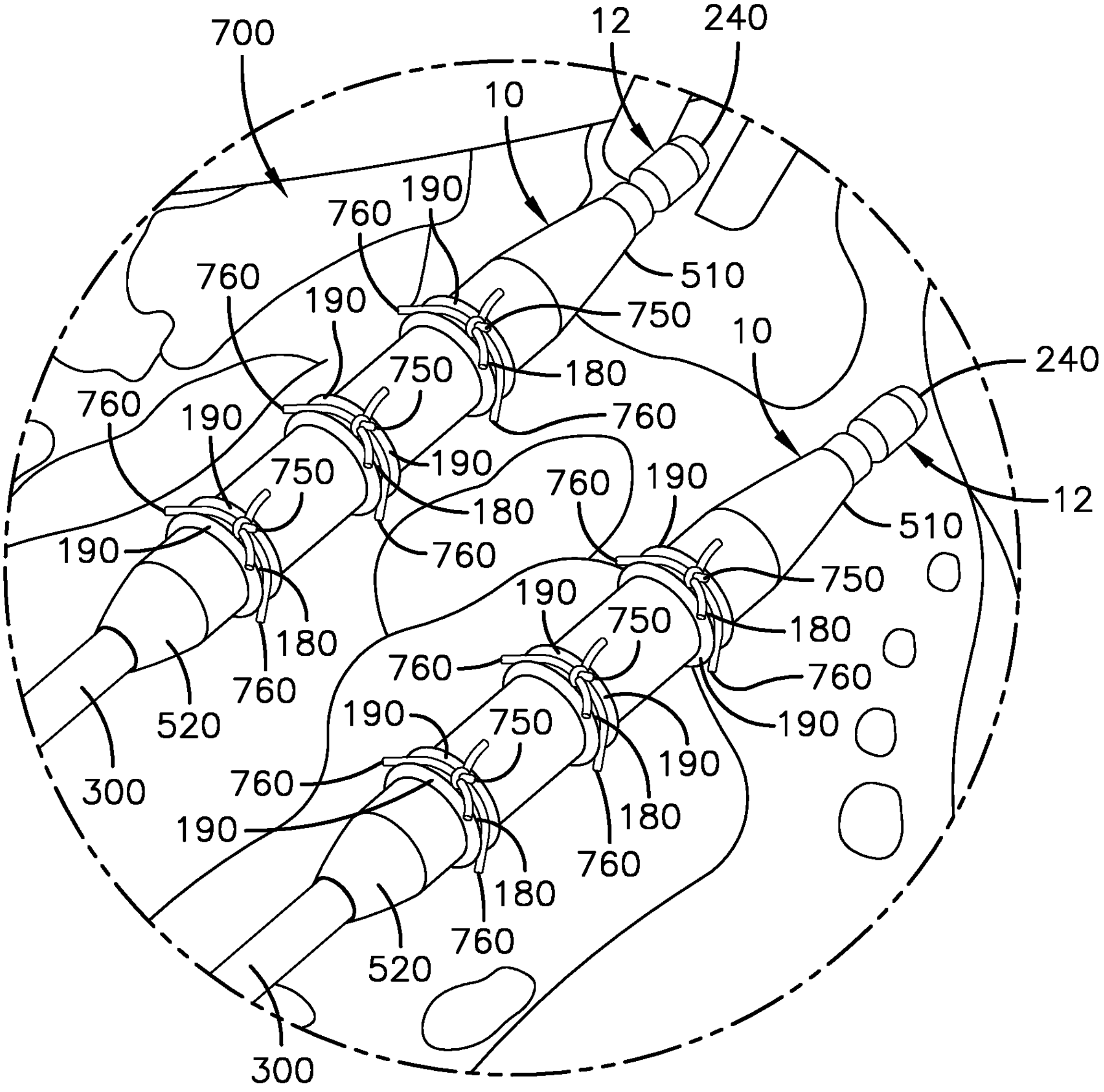
FIG. 6A is an inset view of FIG. 6 showing multiple stimulating members attached to anchors, whereby the anchors are sutured to tissue at the treatment site of implantation in accordance with the various embodiments disclosed herein.

III. Operation:

Thus, in the case of the use of the anchor 10 and the stimulating member 12 in connection with spinal cord stimulation (SCS), the control wires 300 that supply the electrical stimulation signals to the stimulation member 12 are attached to the control unit 310, as shown in FIGS. 6 and 6A. It should be appreciated that one more stimulating members 12 may be utilized, for example 2 stimulating members 12 may be utilized as shown in FIGS. 6 and 6A. Once, the control wires 300 are attached to the control unit 310, the stimulating member 12 is placed into operation, whereby the stimulating member 12 is positioned in the region of a treatment site 700 of implantation in the patient. Thus, in the case of spinal cord stimulation (SCS), the stimulating members 12 are placed near the spinal nerves being treated. Once the stimulating members 12 are positioned at the desired area at the treatment site 700, the anchor 10 is slid over each stimulating member 12, such that the stimulating member 12 is received within the retaining cavity 140 of the anchor 10. As such, the keyed outer surface 160 of the stimulating member 12 and the keyed surface 142 of the retaining cavity 140 mate together. As a result, the stimulating member 12 is secured to the anchor 10 and is prevented from moving relative to the anchor 10. Specifically, the insertion end 240 of the stimulating member 12 is inserted into the opening 140 of the anchor 10. As the stimulating member 12 is urged or slid through the opening 140, the keyed outer surface 160 of the stimulating member 12 engages the keyed surface 142 of the retaining cavity 140. By applying a sufficient amount of force, the stimulating member 12 can be urged or moved through the retaining cavity 140 of the anchor 10, so that it is seated at a desired position within the retaining cavity 140. For example, any amount or length of the stimulating member 12 may be slid into (and in some cases out of) the retaining cavity 140. Accordingly, the stimulating member 12 may be slid through the full extent of the retaining cavity 140, such that the insertion end 240 of the stimulating member 12 extends out of the anchor 10 via the opening 130, as shown in FIG. 6A.

Once the stimulating members 12 are secured to the anchor 10, the anchor 10 is secured in place within the treatment site 700 of implantation by sutures 750, formed of surgical thread, which are received within one or more channels 180. That is, a suture 750 is positioned through tissue 760 at the treatment site 700 of implantation and then positioned so that the suture 750 is wrapped about at least a portion of the channel 180 before the suture 750 is tied off by a knot, as shown in FIG. 6A. Thus, the channel 180 prevents the anchor 10 from slipping from underneath the suture 750, thereby ensuring the anchor 10, and stimulating member 12 carried thereby, do not move or migrate over time from the desired treatment site of implantation 700.

It should be appreciated that the anchor 10 and the stimulating member 12 may be provided together as an unassembled kit. In some embodiments, the anchor 10, the stimulating member 12 and the control unit 10 may be provided as an unassembled kit.

Therefore, it can be seen that the objects of the various embodiments disclosed herein have been satisfied by the structure and its method for use presented above. While in accordance with the Patent Statutes, only the best mode and preferred embodiments have been presented and described in detail, with it being understood that the embodiments disclosed herein are not limited thereto or thereby. Accordingly, for an appreciation of the true scope and breadth of the embodiments, reference should be made to the following claims.

What is claimed is:

1. A kit comprising:

an anchor, wherein said anchor includes:

an elongated body having at least one aperture;

a retaining cavity in fluid communication with said aperture, wherein said retaining cavity has a first keyed shape; and a retaining channel disposed on at least a portion of an outer surface of said body; and a stimulating member, wherein said stimulating member includes a plurality of electrodes, and wherein said stimulating member has a second keyed shape;

wherein said first keyed shape of said anchor and said second keyed shape of said stimulating member are configured to mate together, whereby when the stimulating member is inserted into said aperture, said stimulating member is retained by the retaining cavity of the anchor.

2. The kit of claim 1, wherein said anchor includes another aperture in fluid communication with said retaining cavity.

3. The kit of claim 1, wherein said anchor is formed of flexible material.

4. The kit of claim 1, wherein said retaining cavity has a first section and a second section, wherein said first section has a shape that is different than a shape of said second section.

* * * * *